US 6,511,443 B2

(12) United States Patent
Cuce' et al.

(10) Patent No.: US 6,511,443 B2
(45) Date of Patent: Jan. 28, 2003

(54) MONITORING AND CLASSIFICATION OF THE PHYSICAL ACTIVITY OF A SUBJECT

(75) Inventors: Antonino Cuce', Crema (IT); Maria Cassese, Crema (IT); Davide Platania, Crema (IT)

(73) Assignee: STMicroelectronics, S.r.l., Agrate Brianza (IT)

(*) Notice: Subject to any disclaimer, the term of this patent is extended or adjusted under 35 U.S.C. 154(b) by 65 days.

(21) Appl. No.: 09/825,156

(22) Filed: Apr. 3, 2001

(65) Prior Publication Data

US 2002/0052541 A1 May 2, 2002

(30) Foreign Application Priority Data

Apr. 4, 2000 (EP) .............................................. 00830253

(51) Int. Cl.[7] .................................................. A61B 5/11
(52) U.S. Cl. ......................... 600/595; 128/920; 706/924
(58) Field of Search ................................. 600/587, 595; 123/920, 923, 924, 925; 706/924

(56) References Cited

U.S. PATENT DOCUMENTS

| 5,515,858 | A | * | 5/1996 | Myllymäki | ............... 600/587 |
| 5,788,640 | A | * | 8/1998 | Peters | ........................ 128/920 |
| 6,165,131 | A | * | 12/2000 | Cuce' et al. | ................. 128/920 |
| 6,416,485 | B1 | * | 7/2002 | Rovetta et al. | ............. 600/595 |

FOREIGN PATENT DOCUMENTS

| DE | 4227483 | 11/1993 | ........... A61B/5/103 |
| DE | 19832361 | 2/2000 | ........... A61B/5/00 |
| WO | 86/04802 | 8/1986 | ........... A61B/5/10 |
| WO | 93/16636 | 9/1993 | ........... A61B/5/11 |
| WO | 99/04691 | 2/1999 | ........... A61B/5/113 |

* cited by examiner

*Primary Examiner*—Andrew M. Dolinar
(74) *Attorney, Agent, or Firm*—Lisa K. Jorgenson; Allen, Dyer, Doppelt, Milbrath & Gilchrist, P.A.

(57) ABSTRACT

A portable system carried by a user for assessing movement of the user includes at least one motion sensor adjacent a portion of the user's body under observation. An analog-to-digital converter is connected to the motion sensor for converting an analog signal therefrom into a digital signal. A logic circuit is connected to the analog-to-digital converter for calculating parameters based upon the digital signal. A first fuzzy logic processing circuit is connected to the logic circuit for processing the calculated parameters and for generating corresponding fuzzy classification labels based upon movement of the portion of the user's body under observation during an interval of time. A memory is connected to the first fuzzy logic processing circuit for storing at least one of the calculated parameters and the fuzzy classification labels. A second fuzzy logic processing circuit is connected to the memory for generating an activity index representative of the movement of the user during the interval of time based upon the fuzzy classification labels.

24 Claims, 3 Drawing Sheets

MONITORING AND CLASSIFICATION OF THE PHYSICAL ACTIVITY OF A SUBJECT

FIELD OF THE INVENTION

The present invention relates in general to data acquisition instruments for detecting the motion activity of an individual using and simultaneously correlating the motion activity parameters, such as blood pressure, pulse rate and alike with the detected motion activity.

BACKGROUND OF THE INVENTION

In the medical field it is often useful to monitor patients while they carry on with their daily activities. This permits the correlation of parameters having a clinical interest, such as blood pressure, heart rate, etc., to the actual physical activity being performed during the daily activities. This monitoring and data acquisition is also extremely useful for medical research purposes because it allows more complete data to be obtained as compared to the data obtained in an ambulatory environment under unnatural and/or constricting conditions.

Unfortunately, it is not easy to obtain such measurements if the patient is exerting himself physically since the recorded measurements may provide unreliable data because of the difficulty of correlating the various measurements to the current physical activity. Typically, the patient is recommended to write in a diary the time the daily activities are performed, especially when the carried instrument actually takes a reading. However, this hinders which types of chores the patient may perform, and if these types of chores are performed, this practice may lead to voids and/or imprecisions in the recordings.

The ideal situation would be to combine to the instrument measuring the physiological parameters having a clinical interest with a device capable of automatically detecting the physical activity being performed by the patient. This information would be classified and stored along with the readings periodically taken and recorded. In this way, when the apparatus is given to the patient and properly installed to carry out correct measurements, the patient may indeed lead a normal life without worrying about the measurements being taken.

An approach of this type would be extremely advantageous because of a greatly enhanced reliability of the data. There would be perfect synchronization between the detection and classification of the physical activity being performed and the measurement having a clinical interest. In this way, the parameterization of data as a function of the current state of the physical exertion would be extremely more accurate as compared to the patient who tries to quantify himself in the same physical activities.

This approach would provide all the advantages that only an automatic data acquisition instrumentation can guarantee. It is evident that there is a need and/or utility for an automatic system for detecting and storing parameters representative of the current state of physical exertion of the patient, particularly during prolonged periods of monitoring in a totally instrumental manner without causing discomfort to the monitored patient.

SUMMARY OF THE INVENTION

It is an object of the present invention to provide an automatic system that can be carried or worn by a person for acquiring and recording data on the movement of one or several parts of the person's body. The movement is detected by a corresponding number of sensors placed on respective parts of the person's body so that the motion may be monitored. This fulfils in a optimal manner the above-noted needs and requisites.

Fundamentally, the automatic system according to the invention comprises one or more motion sensors applied to respective parts of the body of the subject being monitored. An analog-digital converter associated with each sensor converts the analog signal generated by the sensor into digital data. A logic block calculates predefined parameters from successive time sequences of the digital data for each sensor.

The automatic system further includes first fuzzy logic means for processing the calculated parameters and for generating corresponding fuzzy logic labels of classification of the motion sensed by each of the sensors during the same time interval of observation. A storage memory stores the parameters and/or fuzzy labels.

Second fuzzy logic processing means are provided for classifying the overall motion activity of the monitored subject based upon the sets of fuzzy labels relative to the different motion sensors, and for outputting an index representing that the physical activity has been performed in the time interval of observation.

The use of fuzzy logic processing is extremely effective because the task is to assess quantities that are difficult to quantify, i.e., fuzzy. This type of processing is greatly enhanced by using fuzzy logic that is ideally structured for managing situations that are not sharply defined.

DETAILED DESCRIPTION OF THE PREFERRED EMBODIMENTS

Figure 1:
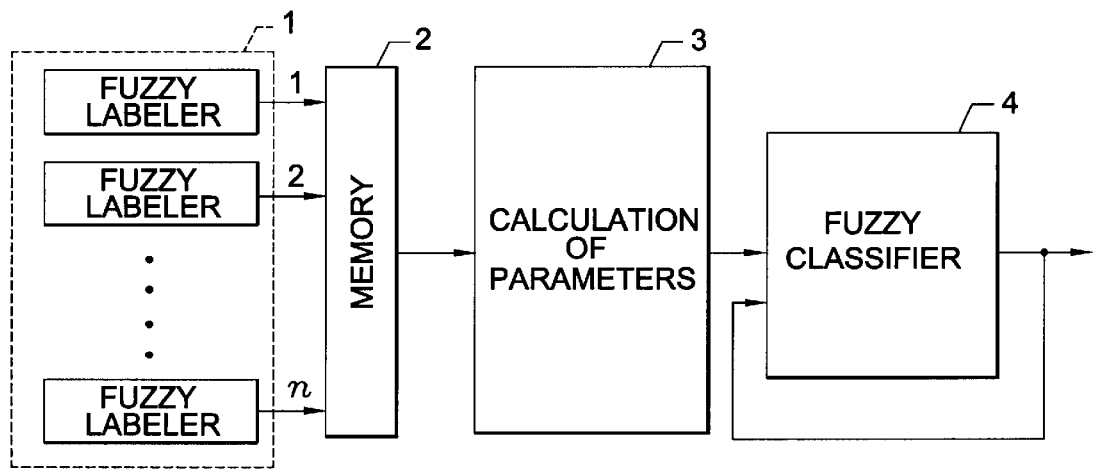
FIG. 1 is a functional block diagram of a system for classifying motion activity according to the present invention.

The system of motion activity classification based on fuzzy logic processing according to the invention is schematically depicted in FIG. 1. The system provides an overall classification of the motion activity of a subject by processing information on simultaneously detected movement of different parts of the subject's body.

In block 1 of FIG. 1, n fuzzy labelers are depicted. Each of them includes a motion sensor and classifies the movement of a certain selected part of the body. Each fuzzy labeler dynamically outputs a sequence of "labels" that forms a classification of the movement detected in a certain time interval T.

For example, the following string may be output:

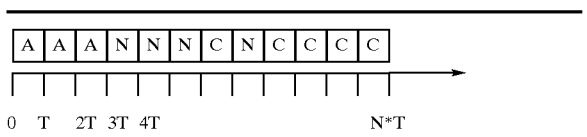

wherein the labels "C", "N" and "A" correspond respectively to a classification of the movement that has been performed in a fixed time interval T as: calm, normal and active or restless. Therefore, in a time N*T, N labels are produced by each of the n labelers.

The monitoring is continuous and information on the motion that has been detected is stored in a memory 2. From information thus obtained on the movement of different parts of the body, several numerical parameters are extracted through a logic processing on the stored data performed by the calculation block 3.

For example, by fixing an interval of time t=N*T, in which as mentioned above N labels of classification are detected for each of the n labelers, significant parameters that may be extracted are the numbers $N_C$, $N_N$ and $N_A$ corresponding to the number of times in which, among the N labels provided by anyone of the n labelers, a classification of movement is obtained. The extracted parameters are then used for carrying out a classification of a "second level" of the motion activity.

The information provided dynamically by the labelers on the instantaneous movement of the different parts of the body, depending on the actual characteristics of the movement performed by the subject to be recognized, as well as the parts of the body that are actually involved, is a classification procedure. Several parameters are established. One is the interval of time t within which the calculation of the desired parameters must be effected is established. The significant parameters for the evaluation are also established.

Finally, the fuzzy algorithm that is implemented in the block 4 is input with the extracted parameters. By applying a certain set of fuzzy rules, the overall motion activity of the subject during the time interval t is classified by processing all the information parameters obtained on the movement of the different parts of the body for the monitored subject during the considered interval of time.

Both the first level movement classification (block 1) and the second level movement classification (block 4) take place dynamically, and the system as a whole is able to monitor the actual motion activity of a subject over long periods of time.

Taking into account that a fuzzy logic algorithm carries out a "weighted average" of the information, it is important to note that by performing a stepwise function the classification of the movement makes the system more versatile, in addition to enhancing reliability. Regardless of the way the overall motion is classified in the block 4 of overall classification, the information on the instantaneous movement of the parts of the body is also processed and stored.

Figure 2:
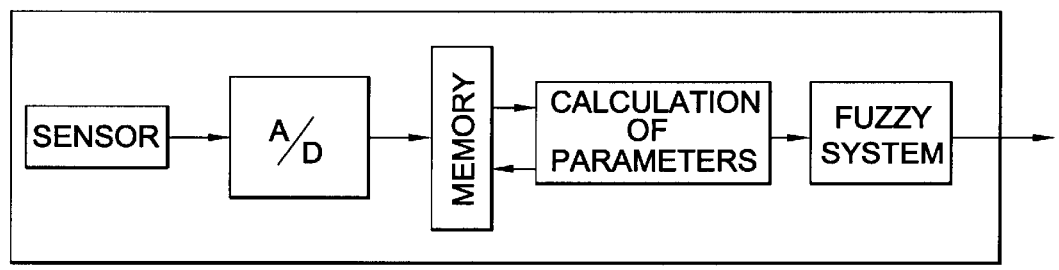
FIG. 2 is a functional block diagram of the fuzzy labeler illustrated in FIG. 1.

The fuzzy labeler will now be discussed in greater detail. A detailed functional diagram of each single labeling device is depicted in FIG. 2. Each device implements a first level classification of the movement. The sensor suitably chosen among the many motion sensors that can be satisfactorily used detects the movement of the part of the body of interest and outputs an analog signal representative of that movement. The analog signal is converted to digital data which is then stored.

After every time interval T that may be chosen by programming, the parameters that will be input to the fuzzy logic algorithm of global classification of the motion activity of the subject are calculated. The fuzzy logic processing block performs a classification of the movement of the particular part of the body as detected during each interval T.

Figure 3:
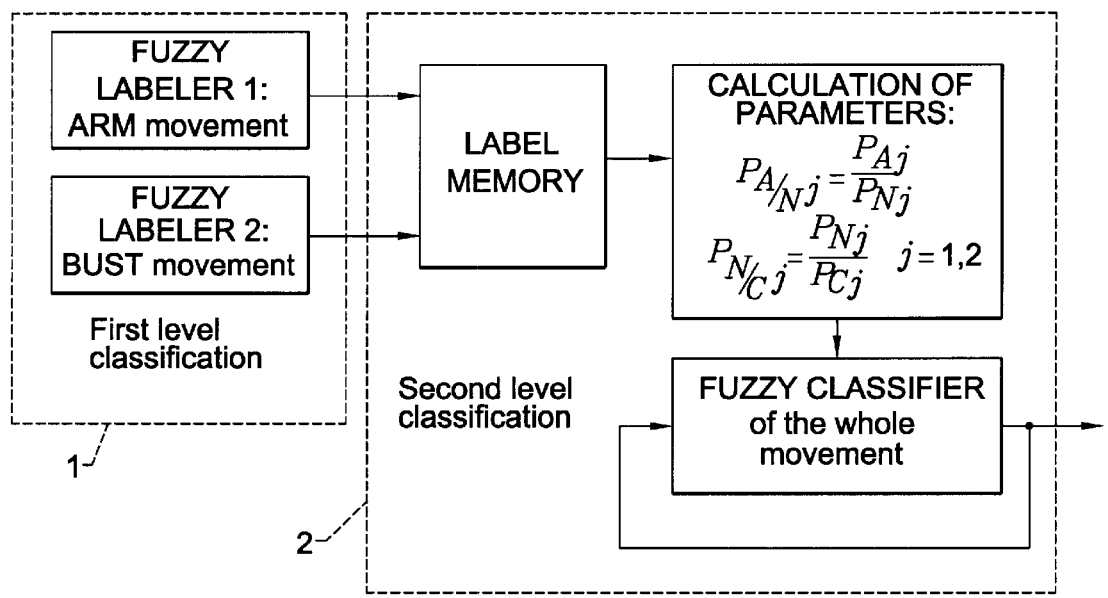
FIG. 3 is a block diagram of the fuzzy logic classification scheme for the motion activity according to one embodiment of the present invention.

According to a sample embodiment that includes a first fuzzy labeler for movement of the right arm and a second fuzzy labeler for movement if the chest, the classifier of the overall motion activity of the invention is schematically depicted in FIG. 3.

The movement classification is done in two steps. Step 1 classifies movement of the single parts of the body (e.g., arm and chest), which is also known as the first level. In this step two labelers are used, one for detecting and classifying movement of the arm and the other for detecting and classifying movement of the chest. Step 2 classifies the overall motion activity of the second level, which is performed by using the information relative to the movement of the chest and arm produced in the first step.

Figure 4:
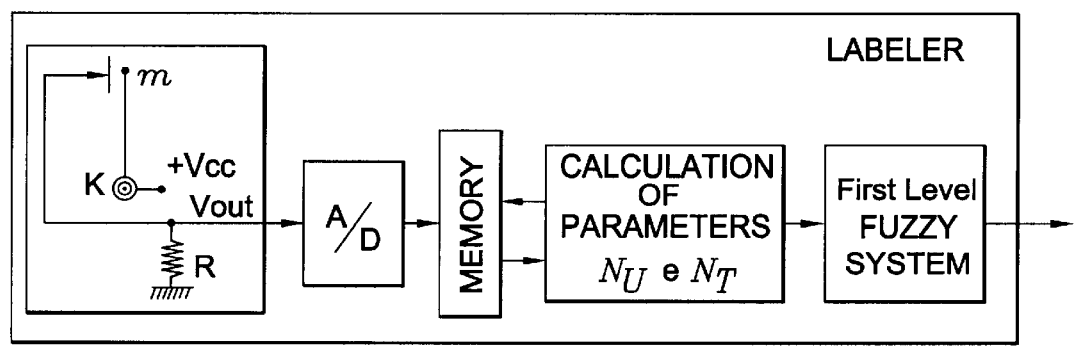
FIG. 4 is a block diagram of the fuzzy labeler illustrated in FIG. 3 supporting the fuzzy logic classification scheme.

The first level classification of the movement of the arm and of the chest will now be discussed in greater detail. Classification of the movement of the arm and of the chest is performed by the block 1 of FIG. 3. Block 1 is formed by two identical fuzzy logic labelers, a detailed diagram of which is depicted in FIG. 4.

The sensor used is formed by a cantilevered lamina restrained by a spring of elastic constant K. The metal lamina closes a circuit every time the system is subjected to an acceleration which overcomes the force of the contrasting spring. The output voltage Vout assumes one of the two values according to whether the lamina closes the circuit. The analog signal provided by such an ON/OFF sensor is converted to a logic signal so that the bits "1" and "0" respectively correspond to the ON and OFF condition of the contact of the circuit of the sensor.

Choosing for example a sampling frequency $f_c$=50 Hz, after every time interval T=5.1 sec. during which a byte is sampled and stored, the calculation of the parameters $N_U$ and $N_T$ according to the following equations is carried out:

$$N_u = \frac{\text{number of 1}}{f_c \cdot T} \quad (1)$$

$$N_T = \frac{\text{number of transitions } 0 \leftrightarrow 1}{f_c \cdot T} \quad (2)$$

Based upon experimentation it has been verified that there is a well defined relationship between the parameters $N_U$ and $N_T$ and the type of corresponding movement. For example, the following results have been obtained. At rest or during calm conditions both parameters $N_U$ and $N_T$ are near zero. The parameter $N_U$ provides a measure of the intensity of the movement. It has been observed that by swinging the arm more and more vigorously, the values of $N_U$ proportionally increase. The parameter $N_T$ increases with the frequency of repeated abrupt movements.

Figure 5:
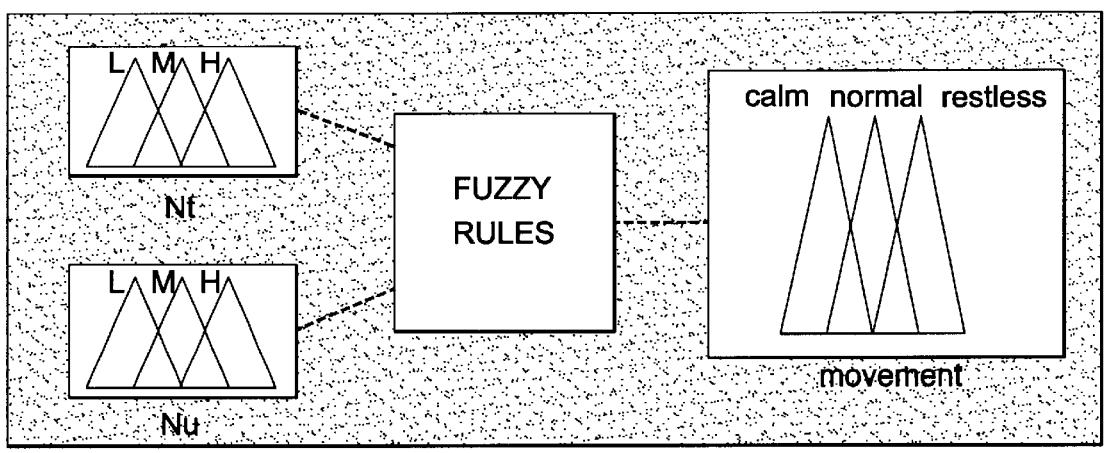
FIG. 5 is a fuzzy logic classification diagram for the motion activity according to the present invention.

The experimental data has permitted the construction of an efficient fuzzy algorithm for classification of the movement of the arm and of the chest based on the parameters $N_U$ and $N_T$. The fuzzy logic processing scheme is illustrated in FIG. 5. Based upon experimental measurements, the value that the parameters $N_U$ and $N_T$ may assume have been grouped in three fuzzy sets corresponding to the indexes: Low, Medium and High. Similarly, movement of the arm and chest have been divided in three fuzzy classes corresponding to: calm (C), normal (N) and active (A).

The fuzzy rules have been defined by contemplating all possible cases. In all the rules, the antecedent contains both input parameters and have contemplated all possible combinations among the fuzzy sets of both parameters. In total, with each variable having 3 membership functions, the block of fuzzy rules contain $3^2=9$ rules of the type:

IF $N_T$ IS Low AND $N_U$ IS Low, THEN movement IS Calm

IF $N_T$ IS Medium AND $N_U$ IS Low, THEN movement IS Calm

IF $N_T$ IS Low AND $N_U$ IS Medium, THEN movement IS Normal etc.

It has been verified that the labeling system thus implemented provides a reliable classification of the movement of even other parts of the body. Of course, by adding other sensors and relative labeling systems, it is possible to generate direct information on the movement of other parts of the body for refining if necessary the monitoring and the precision of the overall assessment of the motion activity of the subject.

Classification of the second level of the overall motion activity will now be discussed in greater detail. The classification of the overall motion activity of the subject is implemented by the block 2 of FIG. 3. This is done by assembling information on movement of the right arm obtained by the two respective identical labeling systems.

After each time interval n*T, where T is the time necessary to receive a classification label, each labeling system outputs a string of the type:

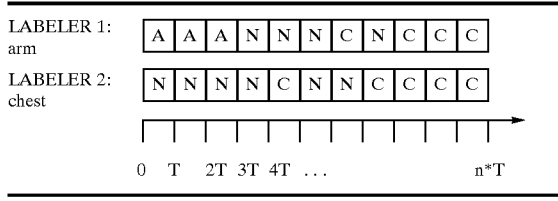

In the example, the interval of time n*T within which the classification is performed has been chosen equal to 1 minute: n*T=12*5.1 sec=1 min. From each string of n labels the following parameters are extracted:

$P_{Cj}$, $P_{Nj}$ and $P_{Aj}$ j=1,2

These parameters respectively represent the number of presences in a string of labels relative to the calm (C), normal (N) and active (A) classification. A different weight is assigned to each count depending on the position of the relative label in the string. The greater the weight is for labels that concentrate in the final portion of the processed string.

The chosen input parameters of the fuzzy logic algorithm of the second level of classification are:

$$P_{\frac{A}{Nj}} = \frac{P_{Aj}}{P_{Nj}} \quad (3)$$

$$P_{\frac{N}{Cj}} = \frac{P_{Nj}}{P_{Cj}} \quad j=1,2 \quad (4)$$

The fuzzy logic algorithm for a second level classification has been developed on the basis of experimental observations and, in particular, the fuzzy sets and the block of rules. In developing the rules, it has been accounted for the fact that different parts of the body contribute in a different way toward an overall assessment of the motion activity of the subject being monitored.

For example, according to a first level classification, should a conspicuously rhythmic movement of the arm and simultaneously a calm condition of the chest be present, the subject would be classified as being in a semi-calm overall condition. Therefore, the fuzzy sets of second level are structured to weight differently the classification or labeling of the movement of different parts of the body.

The values that each parameter may assume are grouped in three fuzzy sets corresponding to Low, Medium and High. The memberships Low, Medium and High are different for each input parameter. In particular, the thresholds that fix the passage from a fuzzy set to another are suitably shifted depending on whether the input parameter refers to the arm or to the chest.

Depending on the values of the input parameters, the block of fuzzy rules classifies the overall motion activity, as calm, normal or active, according to the scheme depicted in FIG. 5. In this step of second level classification, a larger number of parameters must be processed compared to the first level classification. Each fuzzy rule is structured such that the antecedent contains information on both the labelers of the considered example.

The rules are of the type:

IF $P_{A/N^1}$ IS LOW AND $P_{A/N^2}$ IS Low, THEN movement IS Calm

IF $P_{A/N^1}$ IS Medium AND $P_{A/N^2}$ IS Low, THEN movement IS Calm

IF $P_{A/N^1}$ IS LOW AND $P_{A/N^2}$ IS Medium, THEN movement IS Normal etc.

As stated above, the system functions in a dynamic way. Therefore, instant by instant the system produces a classification of the overall motion activity carried out for the n*T preceding seconds.

The prototype system that has been developed has proven itself outstandingly suited to classify the overall motion activity of a subject. Information useful toward a precise characterization of the current state of physical exertion of a patient is provided. The system has been used as a support for a pressure Holter, and the additional information on the motion activity at the time of the taking of each pressure reading reveals itself extremely useful for more reliably analyzing the collected blood pressure data provided by the Holter.

Its principle of operation makes the system of the invention extremely versatile and readily adaptable to different needs. The block of fuzzy rules may be easily reprogrammed, allowing exploitation of additional information on the movement of other parts of the body. In particular, it is possible to obtain instantaneous information on different parts of the body by elaborating which an overall characterization of the physical activity performed during long periods of time to satisfy specific requisites.

That which is claimed is:

1. A portable system carried by a user for assessing body movement, the system comprising:
    at least one motion sensor adjacent a portion of the user's body;
    an analog-to-digital converter connected to said at least one motion sensor for converting an analog signal therefrom into a digital signal;
    a logic circuit connected to said analog-to-digital converter for calculating parameters based upon the digital signal;

first fuzzy logic processing means connected to said logic circuit for processing the calculated parameters and for generating corresponding fuzzy classification labels based upon movement of the portion of the user's body during an interval of time;

a memory connected to said first fuzzy logic processing means for storing at least one of the calculated parameters and the fuzzy classification labels; and second fuzzy logic processing means connected to said memory for generating an activity index representative of the movement of the user during the interval of time based upon the fuzzy classification labels.

2. A portable system according to claim 1, wherein said memory also stores the digital signal from said at least one motion sensor.

3. A portable system according to claim 1, wherein said at least one motion sensor comprises a first motion sensor adjacent an arm of the user and a second motion sensor adjacent a chest of the user.

4. A portable system according to claim 1, wherein said at least one motion sensor detects acceleration in an ON/OFF mode.

5. A portable system according to claim 4, wherein the calculated parameters represent a total time of acceleration and a number of ON/OFF and OFF/ON transitions occurring during the interval of time.

6. A portable system according to claim 1, wherein the fuzzy classification labels qualify movement of the user as either calm, normal or active.

7. A portable system according to claim 1, wherein the activity index qualifies movement of the user as either low, medium or high.

8. A portable system carried by a user for assessing body movement, the system comprising:

at least one motion sensor adjacent a portion of the user's body;

a first fuzzy logic processing circuit connected to said at least one motion sensor for generating fuzzy classification labels based upon movement of the portion of the user's body under observation during an interval of time; and a second fuzzy logic processing circuit connected to said first fuzzy logic processing circuit for generating an activity index representative of the movement of the user during the interval of time based upon the fuzzy classification labels.

9. A portable system according to claim 8, further comprising:

an analog-to-digital converter connected to said at least one motion sensor for converting an analog signal therefrom into a digital signal; and a logic circuit connected to said analog-to-digital converter for calculating parameters based upon the digital signal.

10. A portable system according to claim 9, wherein said first fuzzy processing circuit is connected to said logic circuit for processing the calculated parameters and for generating the corresponding fuzzy classification labels.

11. A portable system according to claim 8, wherein said at least one motion sensor comprises a first motion sensor adjacent an arm of the user and a second motion sensor adjacent a chest of the user.

12. A portable system according to claim 8, wherein said at least one motion sensor detects acceleration in an ON/OFF mode.

13. A portable system according to claim 12, wherein the calculated parameters represent a total time of acceleration and a number of ON/OFF and OFF/ON transitions occurring during the interval of time.

14. A portable system carried by a user for assessing body movement, the system comprising:

a first motion sensor adjacent an arm of the user;

a second motion sensor adjacent a chest of the user;

a logic circuit connected to said first and second motion sensors for calculating parameters based upon respective signals provided by said first and second motion sensors;

a first fuzzy logic processing circuit connected to said logic circuit for processing the calculated parameters and for generating fuzzy classification labels based upon movement of the user's arm and chest under observation during an interval of time; and a second fuzzy logic processing circuit connected to said first fuzzy logic processing circuit for generating an activity index representative of the movement of the user during the interval of time based upon the fuzzy classification labels.

15. A portable system according to claim 14, further comprising:

a first analog-to-digital converter connected to said first motion sensor for converting an analog signal thereform into a digital signal; and a second analog-to-digital converter connected to said second motion sensor for converting an analog signal thereform into a digital signal.

16. A portable system according to claim 15, wherein said logic circuit calculates the parameters based upon the digital signal.

17. A portable system according to claim 14, wherein said first and second motion sensors each detect acceleration in an ON/OFF mode.

18. A portable system according to claim 17, wherein the calculated parameters represent a total time of acceleration and a number of ON/OFF and OFF/ON transitions occurring during the interval of time.

19. A method for assessing body movement of a user carrying a portable system comprising at least one motion sensor adjacent a portion of the user's body, the method comprising:

generating fuzzy classification labels based upon movement of the portion of the user's body during an interval of time using a first fuzzy logic algorithm; and generating an activity index representative of the movement of the user during the interval of time based upon the fuzzy classification labels using a second fuzzy logic algorithm.

20. A method according to claim 19, further comprising:

converting an analog signal from the at least one motion sensor into a digital signal; and calculating parameters based upon the digital signal.

21. A method according to claim 20, wherein the first fuzzy logic algorithm processes the calculated parameters for generating the corresponding fuzzy classification labels.

22. A method according to claim 19, wherein the at least one motion sensor comprises a first motion sensor adjacent an arm of the user and a second motion sensor adjacent a chest of the user.

23. A method according to claim 19, wherein the at least one motion sensor detects acceleration in an ON/OFF mode.

24. A method according to claim 23, wherein the calculated parameters represent a total time of acceleration and a number of ON/OFF and OFF/ON transitions occurring during the interval of time.

* * * * *